United States Patent [19]

Duinker et al.

[11] Patent Number: 4,630,607
[45] Date of Patent: Dec. 23, 1986

[54] APPARATUS FOR THE NON-CONTACT DISINTEGRATION OF STONY OBJECTS PRESENT IN A BODY BY MEANS OF SOUND SHOCKWAVES

[75] Inventors: Simon Duinker, Bloemendaal; Hendrik Mulder, Delft, both of Netherlands

[73] Assignee: N.V. Optische Industrie "De Oude Delft", Netherlands

[21] Appl. No.: 632,209

[22] Filed: Jul. 18, 1984

[30] Foreign Application Priority Data

Jul. 19, 1983 [EP] European Pat. Off. ........ 83201075.5

[51] Int. Cl.$^4$ ............................................... A61B 17/22
[52] U.S. Cl. .................................... 128/328; 128/24 A
[58] Field of Search .............................. 128/24 A, 328

[56] References Cited

U.S. PATENT DOCUMENTS

| 3,269,173 | 8/1966 | Ardenne | 128/660 X |
| 4,526,168 | 7/1985 | Hassler et al. | 128/24 A X |

FOREIGN PATENT DOCUMENTS

| 2418631 | 10/1975 | Fed. Rep. of Germany | 128/24 A |
| 2913251 | 10/1980 | Fed. Rep. of Germany | 128/328 |
| 2140693 | 12/1984 | United Kingdom | 128/24 A |

Primary Examiner—Robert P. Swiatek
Attorney, Agent, or Firm—Louis E. Marn

[57] ABSTRACT

Apparatus for the non-contact disintegration of concrements present in a body by means of sound shockwaves generated in one focus of at least one liquid-filled reflector formed in a reflector block wherein the reflector exhibits rotary symmetry in the form of a semi-ellipsoid (or in the focal line of a toroidal reflector having a semi-elliptical cross-section configuration) and wherein the reflector focuses the sound shockwaves to a second focus and wherein the apparatus further comprises a liquid-filled coupling member connected to the reflector block in a liquid-tight manner. The liquid-filled coupling member is relatively movable to the reflector and can be placed in contact with the skin of the body. The coupling member is of a construction co-axial with the reflector and by axial shifting can be adjusted to the correct depth in the body, and then, in a second adjustment position, the angular position of the reflector can be adjusted so that the reflector axis is caused to coincide with the concrement to be disintegrated.

14 Claims, 6 Drawing Figures

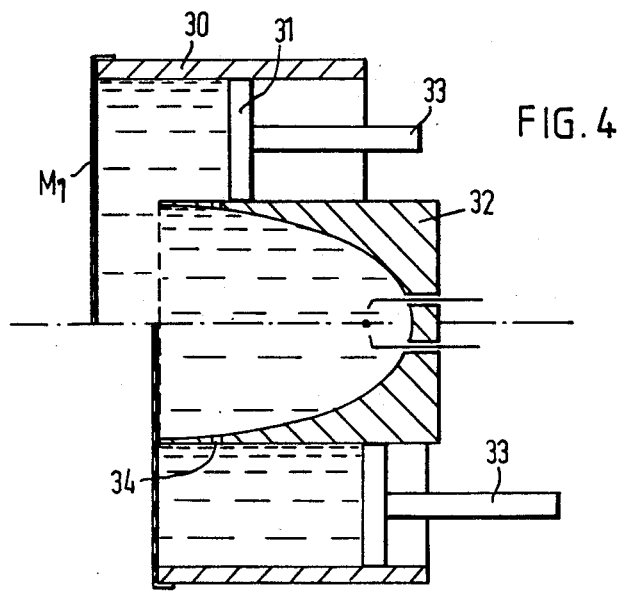
FIG. 4
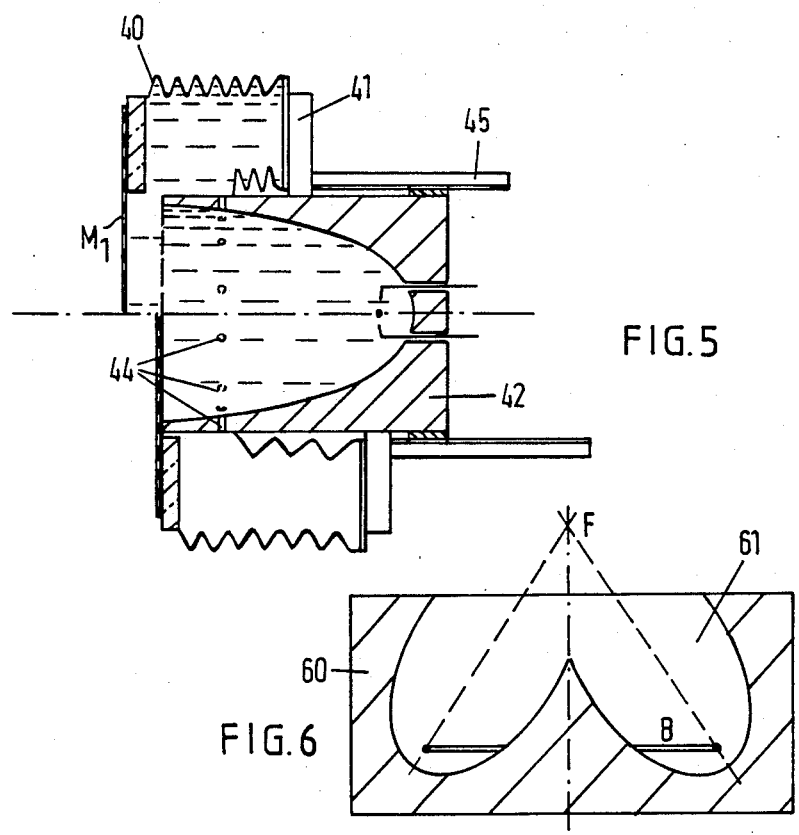
FIG. 5
FIG. 6

APPARATUS FOR THE NON-CONTACT DISINTEGRATION OF STONY OBJECTS PRESENT IN A BODY BY MEANS OF SOUND SHOCKWAVES

The invention relates to an apparatus for the non-contact disintegration of stony objects present in a body by means of sound shockwaves, in which the sound shockwaves are generated in one focus of at least one liquid-filled, rotationally symmetrical reflector having the form of a semi-ellipsoid, or in the focal line of a toroidal reflector having a semi-elliptical cross-sectional configuration, said reflector focussing said sound shockwaves in a second focus.

Such an apparatus is disclosed in German Pat. Nos. 2,351,247 and 2,718,847. These prior devices are designed to disintegrate stony objects present, for example, in the kidneys, the gall or in the bladder of a patient, hereinafter referred to generally as concrements.

In this treatment, in principle, a reflector filled with water or another suitable liquid which adequately transmits the shockwaves to the body can be pressed against the body. This should be effected in such a manner that the second focus of the ellipse coincides with the concrement to be disintegrated. As soon as, however, the prior reflector has been applied in contact with the patient's body, the reflector can no longer be moved in the direction of the long axis of the ellipse, so that, if the second focus does not coincide with the concrement, it is necessary to choose another reflector. As, in addition, in each case the distance between the patient's skin and the concrement is different, it is necessary to have a large number of reflectors, and in each case the correct reflector should be selected empirically.

In order to overcome this problem, an apparatus was designed in the past, which has already been used in practice, and which comprises a bath filled with water, in which the patient is placed. Arranged in the wall or bottom of the bath is the reflector of semielliptical cross-section. By moving the patient in the bath relatively to the reflector, the concrement can be brought into the second focus of the ellipse. Such an apparatus is quite bulky and expensive, and in addition it is not a simple matter to fix a patient accurately in the bath.

In order to avoid the practical drawbacks inherent in immersing patient and reflector in a bath, it has been proposed in German Pat. No. 3,146,626 to couple the reflector by means of a deformable pad to the patient's body, the pad being filled with degased water. In order to prevent the occurrence of undesirable reflections at the side of the body remote from the reflector, it is further proposed in German Pat. No. 3,146,626 to provide an absorbent member at that location in close contact with the body. One disadvantage of this known method is the poor adjustability of the reflector relative to the concrement, in particular as regards the axial adjustment of the reflector, as a result of the undefined dimensional stability of the pad.

It is an object of the present invention to avoid the drawbacks outlined above. More specifically it is an object of the invention to provide an apparatus of the kind described, which makes it possible, without using a bath, to position and arrest a liquid-filled reflector relatively to the patient in a simple manner and so that the concrement coincides with the second focus.

For this purpose, according to the invention, an apparatus of the kind defined in the opening paragraph is provided with a liquid-filled coupling member movable relatively to the reflector and adapted to be placed in contact with the skin of said body, characterized in that said coupling member has a construction co-axial with the reflector, with which, in a first adjustment position, by axial shifting, the second focus of the reflector can be adjusted to the correct depth in the body, and then, in a second adjustment position, the angular position of the reflector can be adjusted so that the reflector axis is caused to coincide with the concrement to be disintegrated, or the other way round.

The invention will be described in more detail hereinafter with reference to the accompanying drawings of some exemplary embodiments.

FIGS. 4 and 5 show a fourth and a fifth embodiment of an apparatus according to the invention.

FIG. 6 shows a variant of the reflector shown in the preceding Figures.

Figure 1:
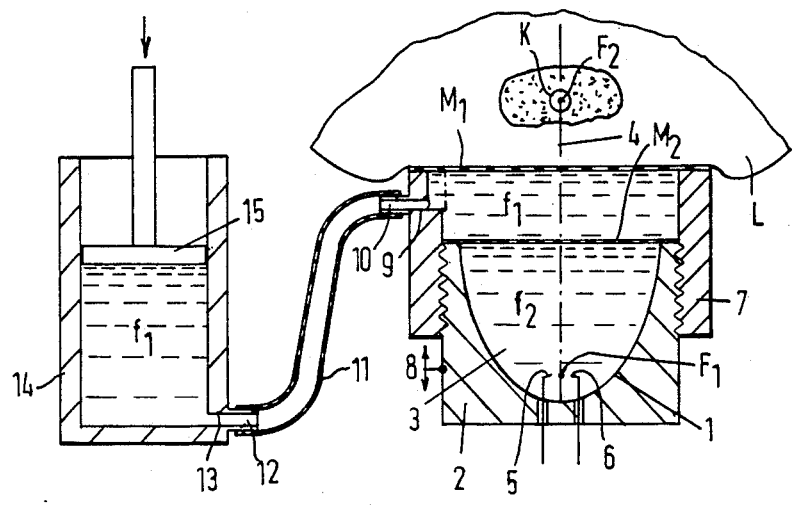
FIG. 1 shows a first embodiment of an apparatus according to the invention.

FIG. 1 shows an ellipsoidal reflector 1 as known per se, for example, from German Pat. No. 2,351,247. The reflector is formed by forming in a block of material 2 a cavity 3 which, in cross-section, has the shape of a semi-ellipse and is rotationally symmetrical about the axis 4. The long axis of the ellipse shape coincides with the axis 4, and this axis contains one of the foci $F_1$ of the ellipse. In this focus ultrasonic shockwaves can be generated in one of the manners known for the purpose. In the present example, two electrodes 5 and 6 are shown diagrammatically for this purpose, which are connected to associated electrical leads, passed to the outside through block 2, and between which a spark discharge can be created.

FIG. 1 further shows a body L, in which a concrement K is present that must be disintegrated. In the correct operative position of reflector 1, the second focus $F_2$ of the ellipse shape falls within the concrement.

In order that this may be accomplished, the block 2 in which the reflector is formed is mounted in a coupling member 7 for movement in the direction of its axis, as indicated by arrows 8. For this purpose block 2 has externally a cylindrical, for example, a right-cylindrical shape, while the coupling member is annular and internally has a shape complementary to block 2. The reflector and the coupling member are filled with liquid to conduct the shockwaves and minimize reflection of the shockwave at the patient's skin. Block 2 should be a sealing fit in the coupling member. For this purpose, if desired, sealing means not shown may be used.

On the side away from reflector block 2, the coupling member is closed with a membrane $M_1$ which in the operative position can be pressed against the patient's skin with a fatty or jelly-like substance being inserted to prevent the entrapment of air and form a good coupling for the shockwaves to be transmitted.

In the embodiment shown in FIG. 1, the coupling member 7 is provided with at least one cross-bore 9, which on the inside of the coupling member, at least in part, terminates in the vicinity of membrane $M_1$. On the outside, a stub tube 10 is provided, to which a liquid conduit 11, for example, a plastic hose is connected, which is in communication with a bore 13, provided with a stub tube 12, in a wall of a liquid container 14.

Extending into the liquid container is a piston 15 whose position is adjustable. Underneath the piston is the same liquid as in the coupling member.

The reflector's position relative to the concrement K can be adjusted by either displacing piston 15, with the reflector block moving along, or moving the reflector block itself, with the piston moving along.

The liquid present within container 14 and in the coupling member may be the same liquid as that present in the reflector cavity. In that case the reflector cavity need not be closed.

It is also possible to provide a first liquid in the reflector cavity and a second liquid in the container and the coupling member. In that case the reflector cavity is sealed with a suitable membrane $M_2$, as shown in FIG. 1. The several liquids are then preferably selected so that the shockwave resistance of the liquid $f_1$ present in the coupling member is intermediate the shockwave resistance of the liquid $f_2$ present in the reflector cavity and the shockwave resistance of the body tissue.

The liquid present in the reflector cavity should satisfy the requirement that the shockwave resistance should deviate as little as possible from the shockwave resistance of the body tissue. If the shockwaves are generated by spark discharge in the liquid, this should further be permitted by the nature of the liquid without any problems.

It is possible that, in order to satisfy both of these requirements, it is preferable to use two different liquids, as described above.

If desired, it is possible to reduce the resistance jump at the interface between the first and the second liquid ($f_1$, $f_2$) or the interface between the liquid $f_1$ and the body tissue still further by using an additional membrane, forming with membrane $M_2$ or membrane $M_1$ a sealed compartment containing a third liquid $f_3$ whose shockwave resistance is intermediate those of the first and the second liquids, or between those of the first liquid and the body tissue.

In order that the position of the reflector may be accurately controlled and monitored, for example, a graduation may be provided on the outside of the reflector block.

It is also possible for the reflector block to be provided with fine external threading cooperating with corresponding internal threading in the coupling member, so that by turning the reflector block about its axis the distance to the patient's skin can be adjusted.

Various other possibilities of adjustment will readily occur to those skilled in the art.

Figure 2:
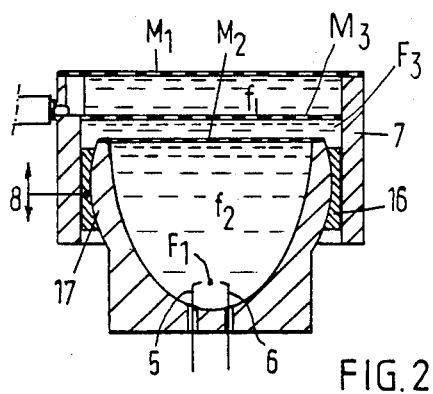
FIG. 2 shows a second embodiment of an apparatus according to the invention.

FIG. 2 shows separately a feature of the invention that in a preferred embodiment may be incorporated in the embodiment shown in FIG. 1. According to FIG. 2, an annular adaptor 16 is provided between the coupling member and the reflector block, the outer wall of which adaptor is a sliding fit in the coupling member, while its inner surface is concave and, together with a portion 17 of the reflector block, of complementary shape, forms a ball joint.

By virtue of this feature, in addition to the correct distance of the reflector from the concrement to be disintegrated, the reflector's angular position relative to the patient's skin can be adjusted, as shown schematically by an arrow 18.

Naturally, various locking means may be provided for fixing the reflector block in a set position. Such locking means can be realized in various ways and will readily occur to those skilled in the art. Such locking means are therefore not shown herein.

Figure 3:
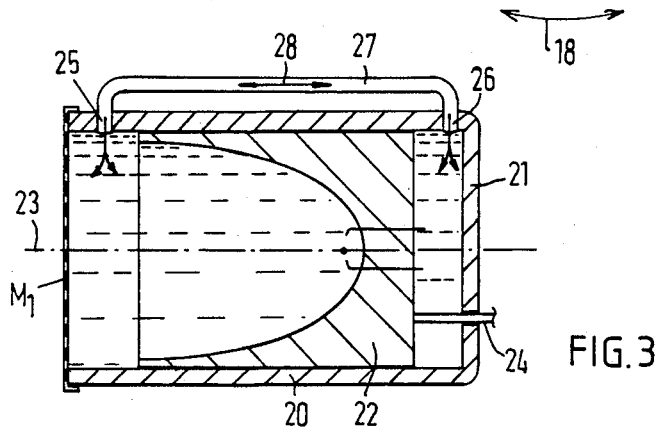
FIG. 3 shows a third embodiment of an apparatus according to the invention.

FIG. 3 shows a different embodiment of a liquid-filled reflector slidingly cooperating with a coupling member.

In this embodiment the coupling member again is a cylindrical container 20 having a fixed end wall 21, the other end wall again being a membrane $M_1$. Placed in the container is a reflector block 22 which can be moved in the direction of axis 23, for example, by means of an operating member 24 connected with the reflector block and extending through end wall 21.

The coupling member and the reflector cavity again contain a liquid, and, as described before, the reflector cavity may contain a different liquid from the coupling member. In this case the reflector cavity is sealed by a second membrane not shown.

Adjacent membrane $M_1$ and adjacent bottom 21, crossbores 25, 26 are formed in the side wall of the cylindrical container 20, which by means of a conduit 27 are interconnected. In this way, as the reflector block is displaced, liquid can flow from the space within the coupling member, on one side of the reflector block, to the space within the coupling member on the other side of the reflector block, as indicated by an arrow 28.

By using a similar adaptor as shown in FIG. 2, and forming the reflector block in a corresponding manner, it is possible to realize a possibility for adjusting the angular position of the reflector block.

FIGS. 4 and 5 show two other embodiments of an apparatus according to the invention. In both cases a reflector block 32, 42 extends at its open end into a wider coupling member 30, 40, respectively, filled with liquid. The coupling member is closed with a member $M_1$ at the end which, in operation, is placed into contact with a patient's skin, and is filled with liquid.

The coupling member 30, 40 has an end wall 31, 41, facing away from membrane $M_1$, and having a central aperture therein, through which the reflector block extends in a sealing manner but so as to permit relative sliding movement. The distance between end wall 31, 41 and the membrane is adjustable.

In the upper half of FIGS. 4 and 5, a situation is shown in which the end wall is relatively close to membrane $M_1$, and in the lower half of FIGS. 4 and 5, a situation is shown in which the end wall is relatively far from membrane $M_1$.

For this purpose, in the embodiment of FIG. 4, this end wall is formed as a piston provided with an operating member 33.

By moving the piston into the direction of membrane $M_1$, the reflector block is moved away from the membrane, and an opposite movement of the piston causes the reflector block to move towards the membrane.

In the embodiment shown in FIG. 5, the coupling member takes the form of a bellows, so that a separate piston is not necessary.

In both cases the reflector cavity may again be closed with a membrane, and different liquids may be used in the reflector cavity and in the coupling member.

If the reflector cavity is not closed with a membrane, the reflector block may be provided adjacent its open end with crossbores 34, 44 to promote rapid re-distribution of the liquid when the end wall is moved.

In both cases the reflector block may be provided on its outside with screw threads cooperating with a suitable threaded bushing abutting against the end wall. The position of the reflector block can be adjusted by turning the bushing. All this is shown diagrammatically by way of example in FIG. 5, in which the threaded bushing is shown at 45.

A possibility of adjusting the angular position of the reflector block is provided for in the embodiment of FIG. 5 in that the bellows is flexible. In the embodiment of FIG. 4, such a possibility of adjustment can be realized similarly to the embodiment of FIG. 2.

The use of a reflector block as shown in FIG. 6 is possible in all embodiments. The reflector block 60 shown in FIG. 6 has a toroidal reflector cavity 61 with an elliptical cross-sectional configuration. There is thus formed a circular focal line B, on which the shockwaves should be generated. The configuration has been selected so that the long axes of all elliptical cross-sections intersect in one point, the focus F. This point is again located outside the reflector block and, in operation, should coincide with the object to be disintegrated.

It is noted that various modifications, in particular of the adjusting and locking means will readily occur to those skilled in the art. Such modifications are considered to fall within the scope of the present invention.

We claim:

1. An apparatus for the non-contact disintegration of a concrement present in a body by means of sound shockwaves, which comprises:

a reflector block having a reflector chamber defining a reflective axis, said reflector chamber being filled with a liquid, said reflector chamber having a surface rotary symmetry in a semi-elliptical cross-sectional configuration defining a first focus for generating sound shockwaves and a second focus for focusing reflected sound waves generated at said first focus;

means for generating said shockwaves at said first focus;

a rigid coupling member disposed on said reflector block for contacting said body, said coupling member being filled with a liquid;

means for axially adjusting said coupling member with respect to said reflector block; and means for angularly adjusting said coupling member with respect to said reflector block, said adjusting means permitting alignment of said second focus to coincide with said concrement present in said body.

2. The apparatus according to claim 1 wherein said coupling member is closed by a first membrane for contacting said body and which, in operation, is accoustically coupled to skin of said body by means of a fatty or jelly-like substance.

3. The apparatus according to claim 2 wherein an end of said coupling member remote from said membrane is closed with a fixed wall through which extends an operating member connected to said reflector block, a sidewall of said coupling member having orifices formed therein adjacent to said membrane and said first wall to provide fluid communication with each other via external tubing.

4. The apparatus according to claim 1 wherein said coupling member is formed so that a volume of said reflector chamber and coupling member is the same in every position thereof.

5. The apparatus according to claim 2 wherein said reflector chamber of said reflector block is closed by a second membrane and is filled with liquid, so that the liquid present in said coupling member is of an acoustic resistance intermediate that of said liquid contained in said reflector chamber and that of body tissue.

6. The apparatus according to claim 5 wherein a third membrane is provided in said coupling member, substantially parallel to said first membrane, and the compartment formed by said third membrane together with said first or said second membrane contains a liquid whose acoustic wave resistance is, respectively, intermediate that of the liquid contained in the coupling member and that of the body tissue, or intermediate that of the liquid contained in the reflector chamber and that of the liquid contained in the rest of the coupling member.

7. The apparatus according to claim 1 wherein said angular adjusting means comprises a ring arranged in said coupling member for sliding movement in a direction of said reflective axis, said ring having a concave surface on an inner surface and connecting with a complementary part of said reflector block to form a ball joint.

8. The apparatus according to claim 1 wherein said coupling member is a resilient bellows.

9. The apparatus according to claim 8 wherein said bellows is comprised of a first portion having an end which, in operation, is remote from said body connected to an outer rim of a flat ring arranged for sliding movement about said reflector block, and a second portion adjacent said inner rim of said flat ring connected to said flat ring and its other end connected to said reflector block.

10. The apparatus according to claim 1 wherein said coupling member, at an end opposite a contacting portion to said body, is closed by an annular piston through which said reflector block extends into said coupling member.

11. The apparatus according to claim 8 or 10 wherein said reflector block is provided adjacent its open end with a plurality of orifices.

12. The apparatus according to claim 1 wherein said reflector block is provided on an outer surface with a screwthread cooperating with a screwthread provided on an inner surface of said coupling member.

13. The apparatus according to claim 1 wherein said reflector block is provided on its outer surface with a screwthread cooperating with a threaded bushing having one end supported on a portion of said coupling member which, in operation, is remote from said body.

14. The apparatus according to claim 1 wherein an orifice is formed in a wall of said coupling member to provide via a conduit fluid communication to a liquid-filled container closed with a piston.

* * * * *